United States Patent
Berkovich

(10) Patent No.: US 9,715,836 B2
(45) Date of Patent: Jul. 25, 2017

(54) TOILET TRAINING ASSEMBLY

(71) Applicant: Linda Berkovich, San Pedro, CA (US)

(72) Inventor: Linda Berkovich, San Pedro, CA (US)

( * ) Notice: Subject to any disclaimer, the term of this patent is extended or adjusted under 35 U.S.C. 154(b) by 205 days.

(21) Appl. No.: 14/633,292

(22) Filed: Feb. 27, 2015

(65) Prior Publication Data

US 2016/0253920 A1    Sep. 1, 2016

(51) Int. Cl.
G09B 19/00    (2006.01)
A47K 11/12    (2006.01)
A61F 5/455    (2006.01)
A47K 13/06    (2006.01)

(52) U.S. Cl.
CPC .......... *G09B 19/0076* (2013.01); *A47K 11/12* (2013.01); *A47K 13/06* (2013.01); *A61F 5/4556* (2013.01)

(58) Field of Classification Search
CPC .... G09B 19/0076; A47K 13/06; A47K 11/12; A61F 5/4556
USPC .............................................. 4/661; 434/247
See application file for complete search history.

(56) References Cited

U.S. PATENT DOCUMENTS

| | | |
|---|---|---|
| 2,699,139 A | 1/1955 | Mackey |
| 2,721,531 A | 10/1955 | Findley, Jr. |
| 2,989,818 A | 6/1961 | Filger et al. |
| 3,172,390 A | 3/1965 | Garthofner |
| D281,193 S | 10/1985 | Chapman |
| 4,883,749 A * | 11/1989 | Roberts ................... A47K 11/04 4/304 |
| 5,369,820 A * | 12/1994 | Blount ................... A47K 11/04 4/483 |
| 5,575,021 A * | 11/1996 | Harris ................... A47K 11/06 4/449 |
| 5,611,092 A * | 3/1997 | Van Dusen ........... A47K 11/06 4/484 |
| 5,685,029 A | 11/1997 | Gee |
| 5,781,939 A * | 7/1998 | Bledsoe ................ A47K 11/04 4/449 |
| 5,842,234 A * | 12/1998 | Dixon .................... A47K 13/06 16/334 |
| 5,926,864 A * | 7/1999 | Lynch .................... A47K 11/04 4/483 |
| 6,430,758 B1 * | 8/2002 | Cabrera ................. A47K 11/06 4/353 |

(Continued)

FOREIGN PATENT DOCUMENTS

WO    WO2006066316    6/2006

*Primary Examiner* — Sam Yao
*Assistant Examiner* — Steven Siebert

(57) ABSTRACT

A toilet training assembly includes a toilet that has a housing, a seat and a lid and the housing has a top wall, a bottom wall and a peripheral wall extending therebetween. The top wall has an opening extending therethrough and the seat is hingedly coupled to the top wall. The seat has an aperture extending therethrough such that the aperture is aligned with the opening. The lid is hingedly coupled to the seat to selectively cover the aperture. A bowl is removably positioned within the opening to capture waste from a child when the child utilizes the toilet to urinate or defecate. A detection apparatus is coupled to the toilet to detect when the waste is deposited in the bowl. The detection apparatus issues an audible congratulation and produces a visual reward when the child deposits the waste in the bowl.

7 Claims, 6 Drawing Sheets

(56) References Cited

U.S. PATENT DOCUMENTS

| | | | |
|---|---|---|---|
| 6,772,454 B1* | 8/2004 | Barry | A47K 11/04 4/661 |
| 6,829,788 B1* | 12/2004 | Allen | A47K 11/06 4/483 |
| 7,237,278 B1* | 7/2007 | Scott | A47K 13/24 4/483 |
| 7,290,296 B1 | 11/2007 | Wilson | |
| 7,891,030 B1* | 2/2011 | Sutton | A47K 11/06 4/483 |
| 8,256,039 B2* | 9/2012 | Morotomi | E03D 9/08 4/443 |
| 2003/0066126 A1* | 4/2003 | Armbruster | A47K 11/06 4/483 |
| 2004/0064884 A1* | 4/2004 | Egeresi | A47K 13/30 4/661 |
| 2010/0146693 A1* | 6/2010 | Yamaguchi | E03D 11/08 4/420 |
| 2011/0119825 A1* | 5/2011 | Reiter | A46B 11/001 4/638 |
| 2012/0297528 A1* | 11/2012 | Petite | A47K 11/06 4/300 |
| 2014/0165311 A1* | 6/2014 | Donegan | A46B 15/0006 15/22.1 |

* cited by examiner

TOILET TRAINING ASSEMBLY

BACKGROUND OF THE DISCLOSURE

Field of the Disclosure

The disclosure relates to toilet devices and more particularly pertains to a new toilet device for providing positive reinforcement while toilet training.

SUMMARY OF THE DISCLOSURE

An embodiment of the disclosure meets the needs presented above by generally comprising a toilet that has a housing, a seat and a lid and the housing has a top wall, a bottom wall and a peripheral wall extending therebetween. The top wall has an opening extending therethrough and the seat is hingedly coupled to the top wall. The seat has an aperture extending therethrough such that the aperture is aligned with the opening. The lid is hingedly coupled to the seat to selectively cover the aperture. A bowl is removably positioned within the opening to capture waste from a child when the child utilizes the toilet to urinate or defecate. A detection apparatus is coupled to the toilet to detect when the waste is deposited in the bowl. The detection apparatus issues an audible congratulation and produces a visual reward when the child deposits the waste in the bowl.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
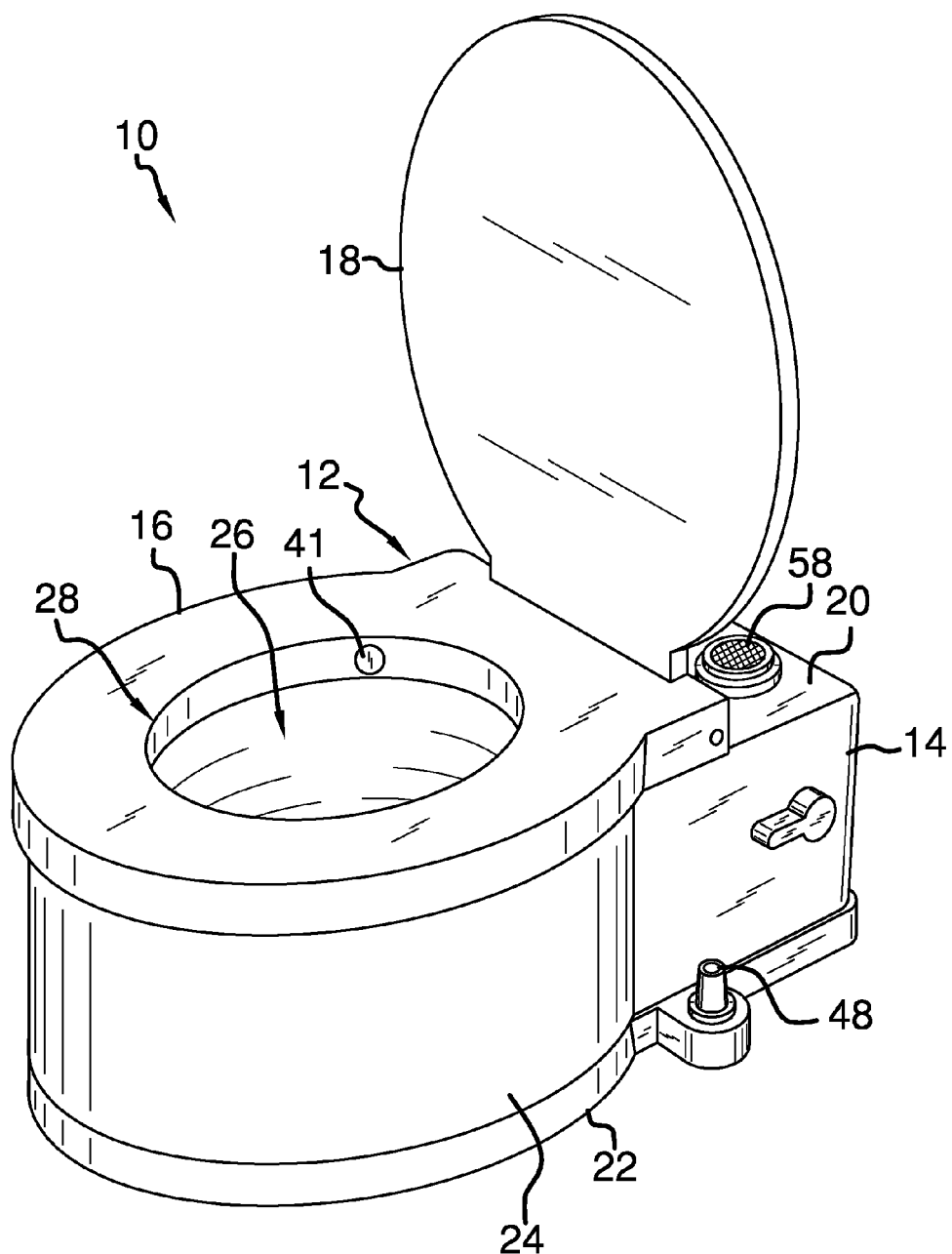
FIG. 1 is a top perspective view of a toilet training assembly according to an embodiment of the disclosure.
Figure 2:
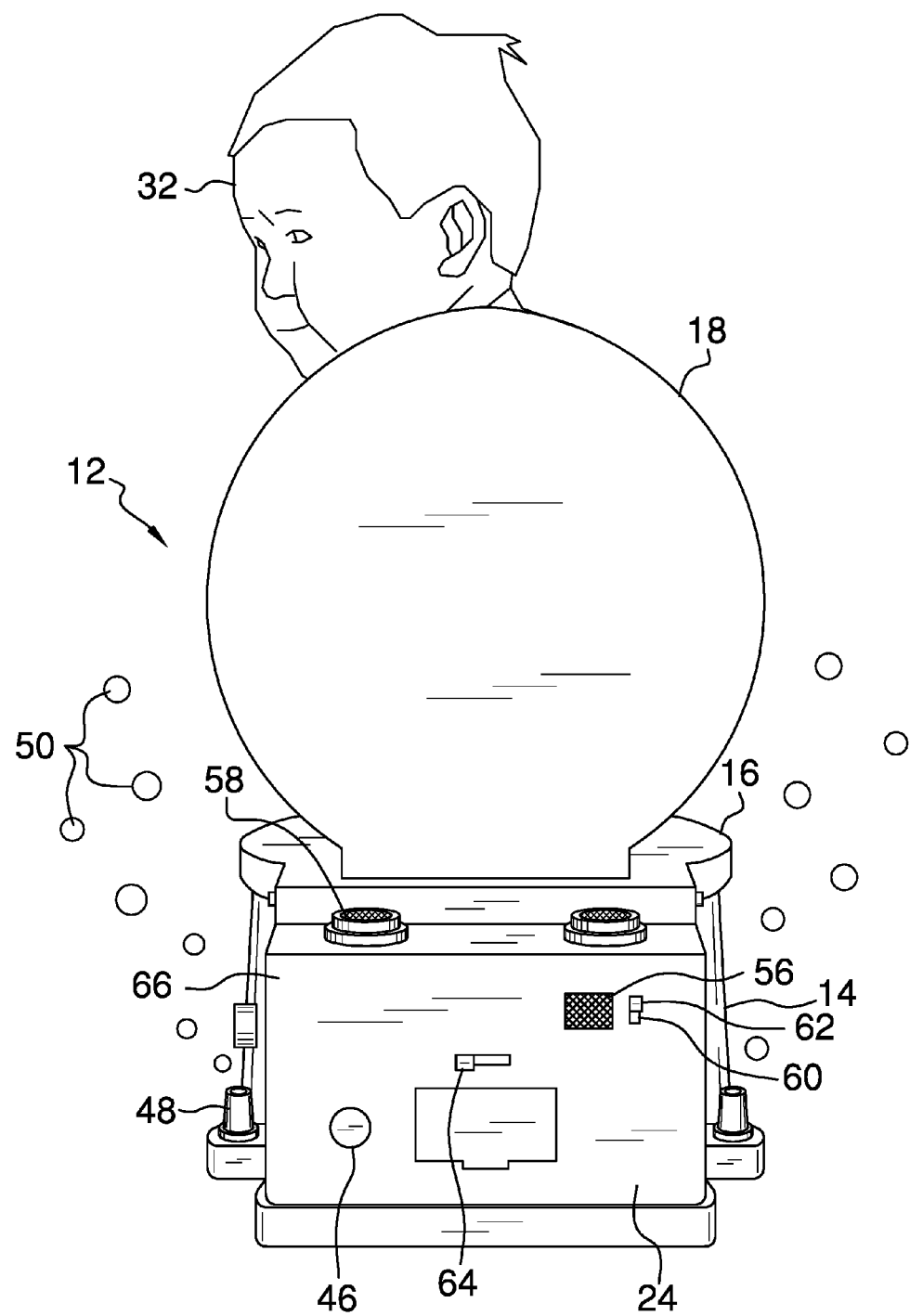
FIG. 2 is a back view of an embodiment of the disclosure.
Figure 3:
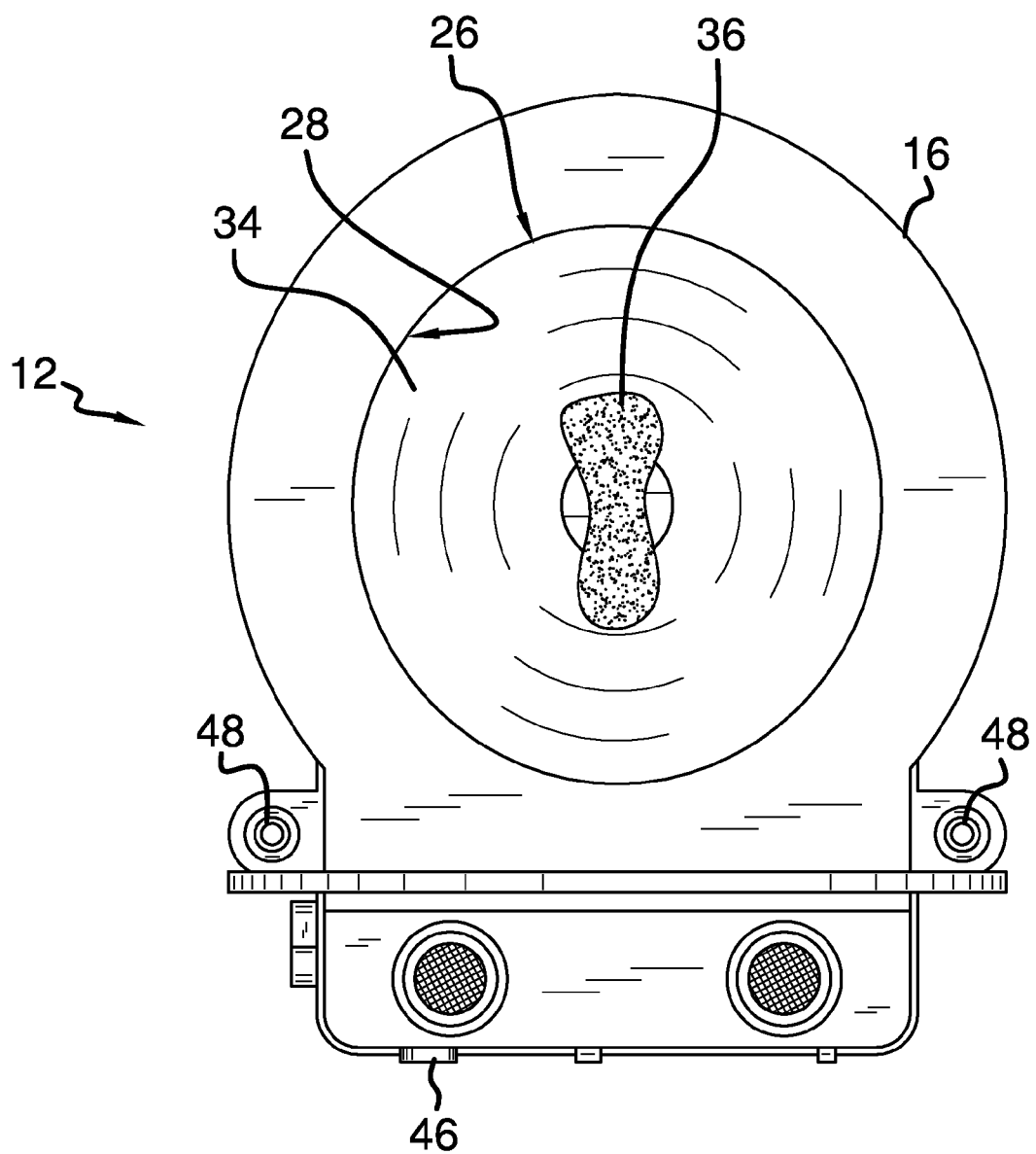
FIG. 3 is a top view of an embodiment of the disclosure.
Figure 4:
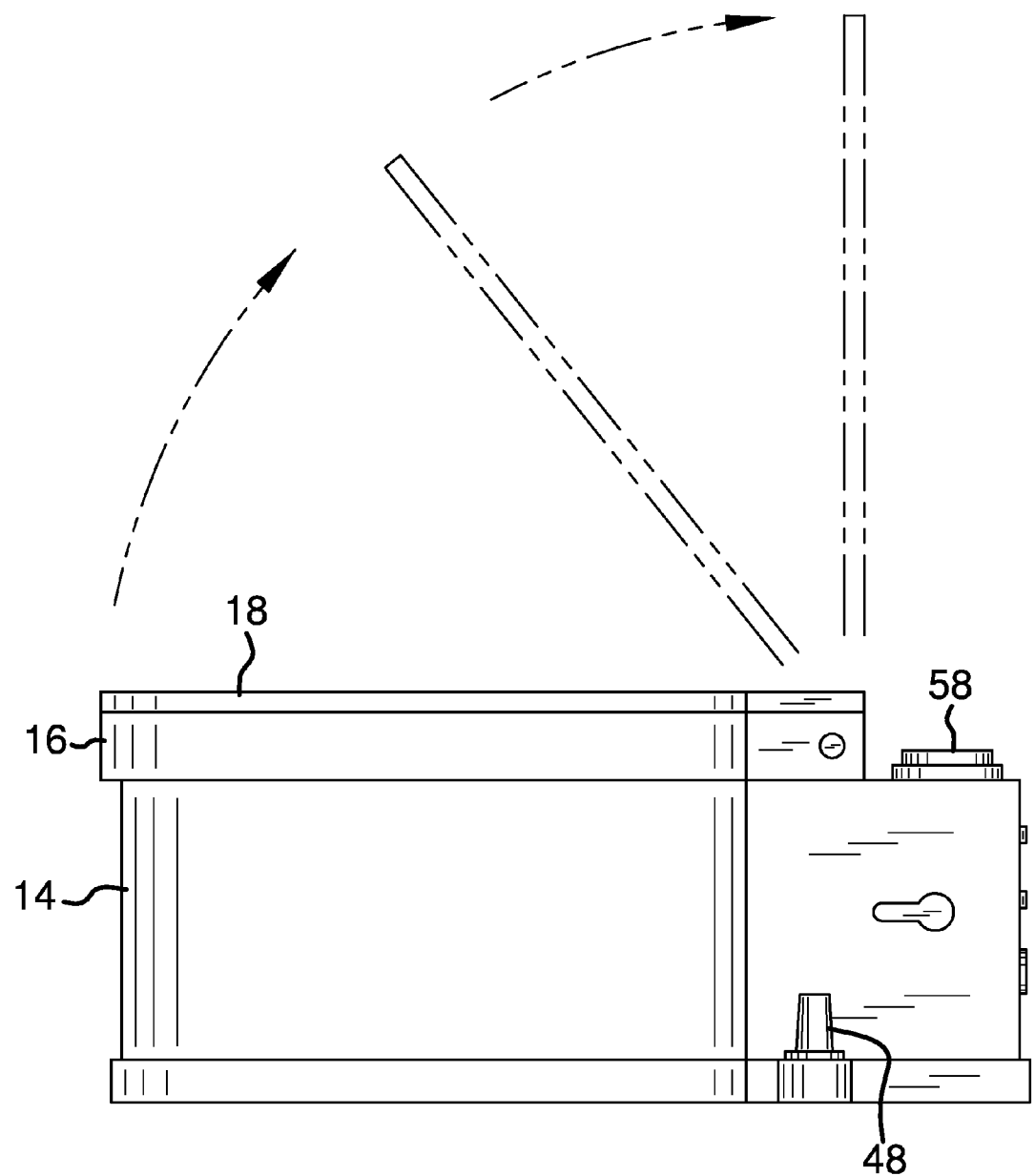
FIG. 4 is a left side view of an embodiment of the disclosure.
Figure 5:
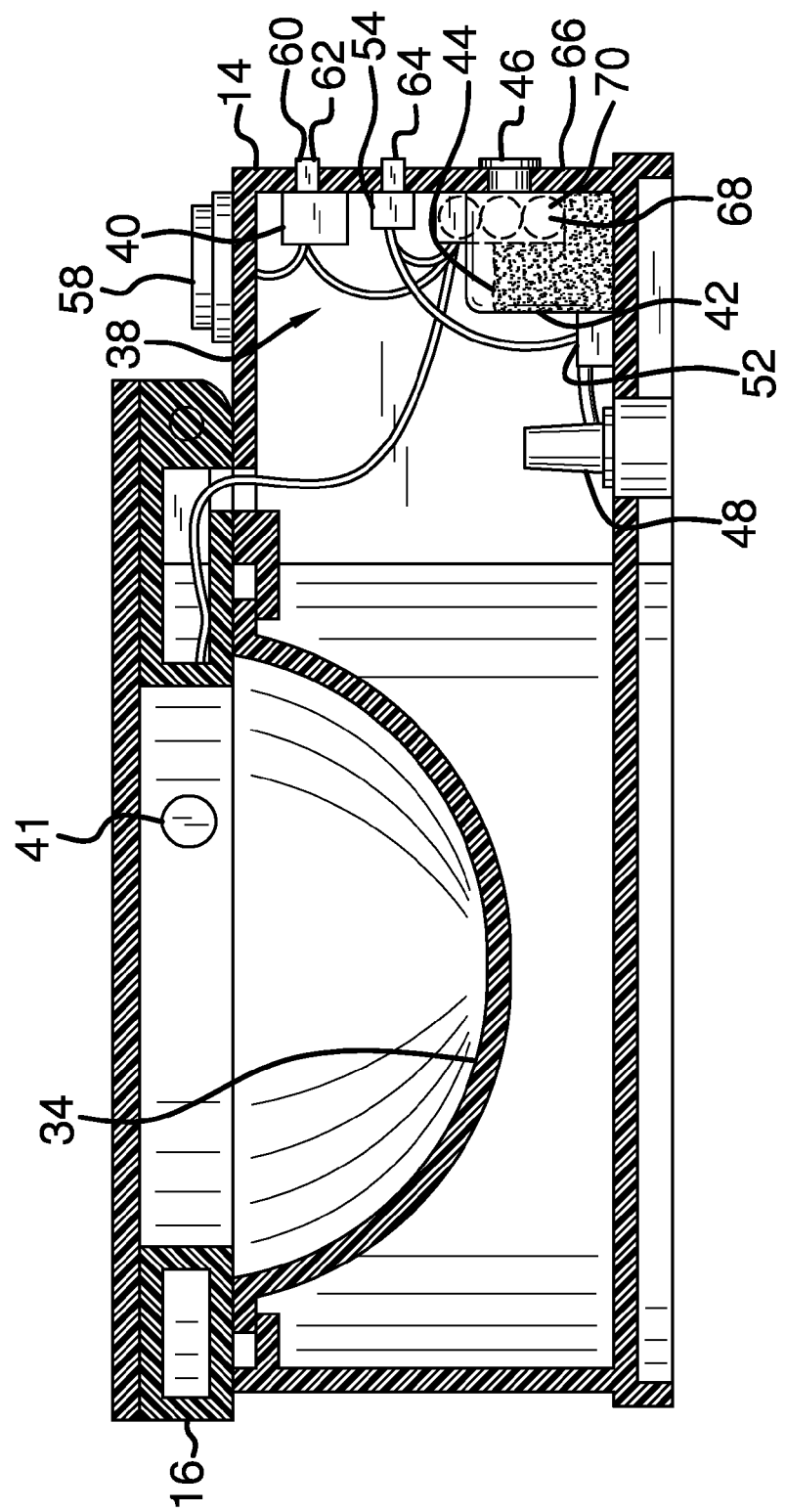
FIG. 5 is a cross sectional view taken along line 5-5 of FIG. 1 of an embodiment of the disclosure.
Figure 6:
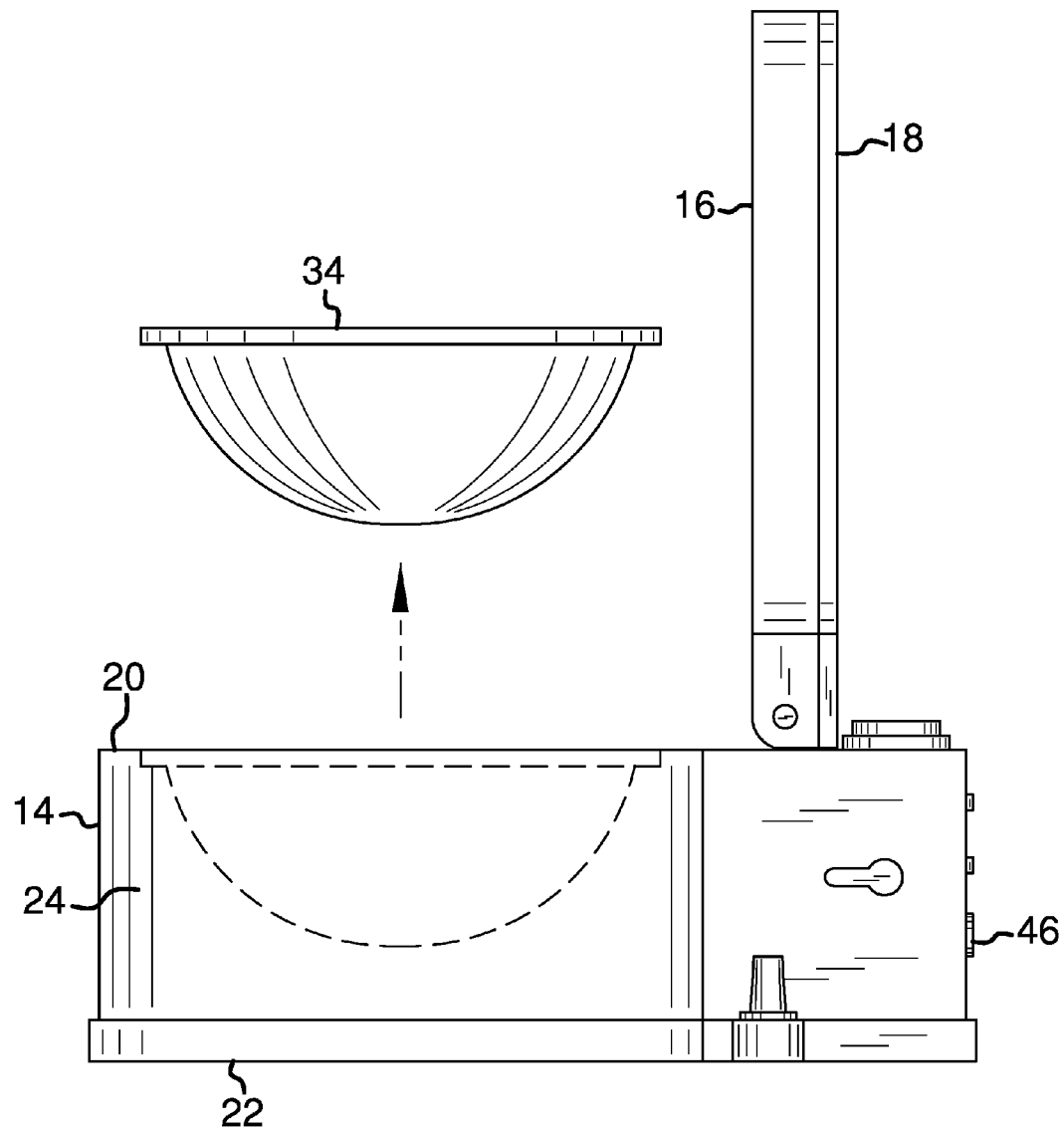
FIG. 6 is a left side perspective view of an embodiment of the disclosure.

With reference now to the drawings, and in particular to FIGS. 1 through 6 thereof, a new toilet device embodying the principles and concepts of an embodiment of the disclosure and generally designated by the reference numeral 10 will be described.

As best illustrated in FIGS. 1 through 6, the toilet training assembly 10 generally comprises a toilet 12 that has a housing 14, a seat 16 and a lid 18 and the 14 housing has a top wall 20, a bottom wall 22 and a peripheral wall 24 extending therebetween. The top wall 20 has an opening 26 extending therethrough and the seat 16 has an aperture 28 extending therethrough. The aperture 28 is centrally positioned on the seat 16. The seat 16 is hingedly coupled to the top wall 20, aligning the aperture 28 with the opening 26. The lid 18 is hingedly coupled to the seat 16 to selectively cover the aperture 28. A child 32 may sit upon the seat 16 to practice toilet training. A bowl 34 is removably positioned within the opening 26 to capture waste 36 from the child 32 when the child 32 utilizes the toilet 12 to urinate or defecate.

A detection apparatus 38 is coupled to the toilet 12 to detect when the waste 36 is deposited in the bowl 34. The detection apparatus 38 may issue an audible congratulation and may produce a visual reward when the child 32 deposits the waste 36 in the bowl 34. The detection apparatus 38 comprises a control circuit 40 positioned within the housing 14. A sensor 41 is coupled to the toilet and is electrically coupled to the control circuit 40 to detect the presence of the waste 36 in the bowl 34. The sensor 41 may comprise a weight sensor or the like.

A fluid reservoir 42 is positioned within the housing 14 to contain a fluid 44. The fluid 44 may be a solution of soap and water or the like. Moreover, the fluid 44 is utilized in the convention of blowing bubbles. A fill spout 46 extends from the fluid reservoir 42 outwardly through the peripheral wall 24. The fill spout 46 is utilized to fill the fluid reservoir 42 with the fluid 44.

A nozzle 48 is coupled to the housing 14 and is in fluid communication with the fluid reservoir 42. The nozzle 48 is electrically coupled to the control circuit 40 to produce bubbles 50 when the sensor 41 detects the waste 36 in the bowl 34. The nozzle 48 includes a pump 52 to urge the fluid 44 from the fluid reservoir 42 and outwardly from the nozzle 48 in the form of the bubbles 50. The pump 52 is electrically coupled to the control circuit 40. The nozzle 48 may be one of a pair of nozzles 48 and each of the nozzles 48 may be positioned on opposing sides of the peripheral wall 24 of the housing 14.

An electronic memory 54 is positioned within the housing 14 and is electrically coupled to the control circuit 40 to store an audio message. The electronic memory 54 may comprise RAM of any conventional design. A microphone 56 is coupled to the housing 14 and is electrically coupled to the electronic memory 54 to record the audio message, storing the audio message in the electronic memory. The audio message may be a congratulatory statement or the like. A speaker 58 is coupled to the housing 14 and is electrically coupled to the control circuit 40 to emit the audio message when the sensor 41 detects the waste 36 in the bowl 34. The speaker 58 may be positioned on the top wall 20 of the toilet 12. Moreover, the speaker 58 may be one of a pair of speakers 58 positioned on opposing sides of the top wall 20.

An actuator 60 is coupled to the housing 14 and is electrically coupled to the control circuit 40 to actuate and de-actuate the control circuit 40. The actuator 60 may comprise a record actuator 62 and an on/off actuator 64 each positioned on a back side 66 of the peripheral wall 24. The record actuator 62 may actuate the microphone 56 to record the audio message. A power supply 68 is positioned within the housing 14 and is electrically coupled to the on/off actuator 64. The power supply 68 may comprise at least one battery 70.

In use, the record actuator 62 is actuated to record the audio message. The fluid 44 is poured into the fill spout 46 to fill the fluid reservoir 42. The on/off actuator 64 is actuated to actuate the control circuit 40. The nozzle 48 blows the bubbles 50 and the speaker 58 emits the audio message when the child 32 properly utilizes the toilet 12 to defecate or urinate. The bubbles 50 and the audio message provide positive reinforcement during toilet training. The bowl 34 is removed from the housing 14 to be emptied after the child 32 has properly utilized the toilet 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A toilet training assembly configured to toilet train a child, said assembly comprising:
   a toilet having a housing, a seat and a lid, said housing having a top wall, a bottom wall and a peripheral wall extending therebetween, said top wall having an opening extending therethrough, said seat being hingedly coupled to said top wall, said seat having an aperture extending therethrough such that said aperture is aligned with said opening, said lid being hingedly coupled to said seat, said lid covering said aperture;
   a bowl removably positioned within said opening, said bowl being configured to capture waste from the child when the child utilizes said toilet to urinate or defecate;
   a detection apparatus coupled to said toilet, said detection apparatus being configured to detect when the waste is deposited in said bowl, said detection apparatus issuing an audible congratulation and producing a visual reward when the child deposits the waste in said bowl, said detection apparatus including a control circuit positioned within said housing;
   a sensor coupled to said toilet, said sensor being electrically coupled to said control circuit, said sensor being configured to detect the waste in said bowl;
   a fluid reservoir positioned within said housing, said fluid reservoir being configured to contain a fluid; and
   a nozzle coupled to said housing, said nozzle being in fluid communication with said fluid reservoir, said nozzle being electrically coupled to said control circuit, said nozzle being configured to produce bubbles when said sensor detects the waste in said bowl, said nozzle being directed outwardly from said housing such that said nozzle is configured for producing the bubbles adjacent to the child while the child is on said seat.

2. The assembly according to claim 1, further comprising an electronic memory positioned within said housing, said electronic memory being electrically coupled to said control circuit, said electronic memory being configured to store an audio message.

3. The assembly according to claim 2, further comprising a microphone coupled to said housing, said microphone being electrically coupled to said electronic memory, said microphone being configured to record the audio message such that the audio message is stored in said electronic memory.

4. The assembly according to claim 3, further comprising a speaker coupled to said housing, said speaker being electrically coupled to said control circuit, said speaker being configured to emit the audio message when said sensor detects the waste in said bowl.

5. The assembly according to claim 1, further comprising an actuator coupled to said housing, said actuator being electrically coupled to said control circuit to actuate and de-actuate said control circuit.

6. The assembly according to claim 5, further comprising a power supply positioned within said housing, said power supply being electrically coupled to said actuator, said power supply comprising at least one battery.

7. A toilet training assembly configured to toilet train a child, said assembly comprising:
   a toilet having a housing, a seat and a lid, said housing having a top wall, a bottom wall and a peripheral wall extending therebetween, said top wall having an opening extending therethrough, said seat being hingedly coupled to said top wall, said seat having an aperture extending therethrough such that said aperture is aligned with said opening, said lid being hingedly coupled to said seat, said lid covering said aperture;
   a bowl removably positioned within said opening, said bowl being configured to capture waste from the child when the child utilizes said toilet to urinate or defecate;
   a detection apparatus coupled to said toilet, said detection apparatus being configured to detect when the waste is deposited in said bowl, said detection apparatus issuing an audible congratulation and producing a visual reward when the child deposits the waste in said bowl, said detection apparatus comprising:
     a control circuit positioned within said housing;
     a sensor coupled to said toilet, said sensor being electrically coupled to said control circuit, said sensor being configured to detect the waste in said bowl;
     a fluid reservoir positioned within said housing, said fluid reservoir being configured to contain a fluid;
     a nozzle coupled to said housing, said nozzle being in fluid communication with said fluid reservoir, said nozzle being electrically coupled to said control circuit, said nozzle being configured to produce bubbles when said sensor detects the waste in said bowl, said nozzle being directed outwardly from said housing such that said nozzle is configured for producing the bubbles adjacent to the child while the child is on said seat;
     an electronic memory positioned within said housing, said electronic memory being electrically coupled to said control circuit, said electronic memory being configured to store an audio message;
     a microphone coupled to said housing, said microphone being electrically coupled to said electronic memory, said microphone being configured to record the audio message such that the audio message is stored in said electronic memory;
     a speaker coupled to said housing, said speaker being electrically coupled to said control circuit, said speaker being configured to emit the audio message when said sensor detects the waste in said bowl;
an actuator coupled to said housing, said actuator being electrically coupled to said control circuit to actuate and de-actuate said control circuit; and
a power supply positioned within said housing, said power supply being electrically coupled to said actuator, said power supply comprising at least one battery.

* * * * *